(12) United States Patent
Shabaan et al.

(10) Patent No.: US 11,851,399 B1
(45) Date of Patent: Dec. 26, 2023

(54) DISELENIDE-BASED ORGANIC PROTECTIVE FILMS

(71) Applicant: KING FAISAL UNIVERSITY, Hofouf (SA)

(72) Inventors: Saadeldin Elsayed Ibrahim Shabaan, Hofouf (SA); Hany Mohamed Abd El-Lateef Ahmed, Hofouf (SA); Mai Mostafa Khalaf Ali, Hofouf (SA); Mohamed Gouda, Hofouf (SA)

(73) Assignee: KING FAISAL UNIVERSITY, Hofouf (SA)

( * ) Notice: Subject to any disclaimer, the term of this patent is extended or adjusted under 35 U.S.C. 154(b) by 0 days.

(21) Appl. No.: 18/078,630

(22) Filed: Dec. 9, 2022

(51) Int. Cl.
*C07C 391/02* (2006.01)
*C03B 37/10* (2006.01)

(52) U.S. Cl.
CPC ............ *C07C 391/02* (2013.01); *C03B 37/10* (2013.01)

(58) Field of Classification Search
None
See application file for complete search history.

(56) References Cited

U.S. PATENT DOCUMENTS

2020/0369912 A1    11/2020    Qian et al.

FOREIGN PATENT DOCUMENTS

CN        112341758 A       2/2021
WO        2019086140 A1     5/2019

OTHER PUBLICATIONS

Diaz et al., Synthesis and Leishmanicidal Activity of Novel Urea, Thiourea, and Selenourea Derivatives of Diselenides. Antimicrobial Agents and Chemotherapy, 2019, 63, p. 1-16.*
Zhang, F., et al., "Self-healing mechanisms in smart protective coatings: A review," Corrosion Science, 144: pp. 74-88 (Aug. 21, 2018).

* cited by examiner

*Primary Examiner* — Po-Chih Chen
(74) *Attorney, Agent, or Firm* — Nath, Goldberg & Meyer; Richard C. Litman

(57) ABSTRACT

A diselenide protective film, a method of using the diselenide protective film, and a method of making the diselenide protective film are provided. The diselenide protective film includes at least one of three novel diselenide organic polymer structures, and the film provides protection against corrosion of metals such as steel. The method of making the diselenide protective film comprising at least one of three novel diselenide organic polymer structures includes reacting a diselenide-based diamine with one of a diisocyanate, a diisocyanate and phosgene, or a diisocyanate, epichlorohydrin and potassium hydroxide.

17 Claims, No Drawings

DISELENIDE-BASED ORGANIC PROTECTIVE FILMS

BACKGROUND

1. FIELD

The disclosure of the present patent application relates to diselenide-based self-healing protective coating films effective for protecting against metal and metal alloy corrosion, such as acidic steel corrosion.

2. DESCRIPTION OF THE RELATED ART

It is known in the art generally that various metals are prone to corrosion, with steel or steel alloys in particular being subject to potential acidic corrosion. In general, self-healing coatings are considered as one route for efficient anti-corrosion protection while maintaining a low demand for cathodic protection. Such coatings typically incorporate micro- or nano-capsules that contain film-formers able to repair the coating damage when the coating is scratched.

The application of coatings is the most popular strategy for preventing abrasion or other corrosion on steel and steel alloys. Due to these compounds' active corrosion protection properties, chromate-based conversion coatings and paints have been used to shield steel surfaces from corrosion. Chromate-based coatings, however, are being abandoned due to their high toxicity and carcinogenicity. As a result, there is an increasing need for chromate-free, environmentally safe passable anti-erosion pre-treatments.

Due to their adaptability and inexpensive price, organic coatings with polymers are one potential alternative for preventing steel or other metal corrosion. When such coatings are used, the metal and the hostile media are separated by an isolating preservation layer provided by the organic coatings. If the corrosive environment changes or an external factor affects the active interface, self-healing anti-corrosion coatings can repair the produced clefts. Commonly, polymerized components are put into nano/micro containers or encapsulants to provide this functionality, which are then dispersed throughout the coating.

Polymer matrices are well known for their stability and anti-corrosive properties (Barsoum and Barsoum, 2002; Kim et al., 2019). The addition of different kinds of nanoparticles to polymeric coatings improves the coating's anti-corrosive response (Shi et al., 2009) and enables new features such as low electric resistance or self-healing properties (Tiwari et al., 2014). These new features expand the range of applications, service-life and brings innovative solutions to this well-developed market.

However, the current organic polymer coatings have the problems that they require extra materials such as nanoparticles, may not provide adequate corrosion resistance, and may have a higher cost than the ecologically undesirable and toxic chromate coatings and the like.

Thus, additional protective coatings for metals, particularly steel or steel alloys, are desired for superior anticorrosion effectiveness, low toxicity, easy production, and lower cost while also maintaining a low demand for cathodic protection.

SUMMARY

The present subject matter relates to diselenide-based organic protective film coatings effective for protecting against metal and metal alloy corrosion, such as acidic steel corrosion. In one embodiment, these diselenide-based organic protective film coatings may include polyurea, polyurethane, and epoxy resin and may be used as protective coating films to prevent, inhibit or reduce metal corrosion.

In one embodiment, the present protective films can be synthesized from a diselenide-based diamine and one of: commercially available diisocyanates, diselenide diisocyanates and phosgene, or diisocyanates with epichlorohydrin in the presence of potassium hydroxide.

In this regard, an embodiment of the present subject matter relates to a diselenide protective film comprising a diselenide polymer structure selected from the group consisting of

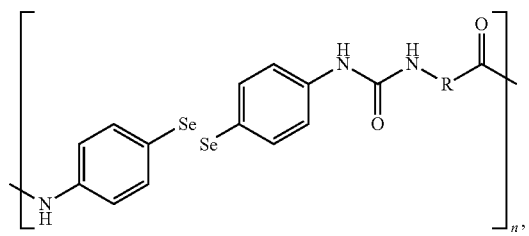

wherein each R is selected from the group consisting of any of the following structures:

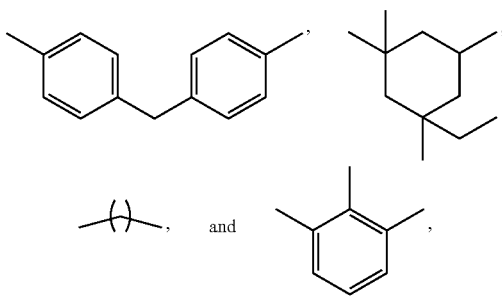

and wherein n is any integer; and

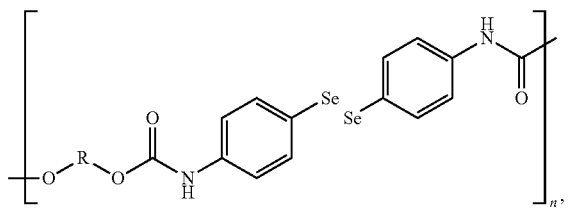

wherein each R is selected from the group consisting of any of the following structures:

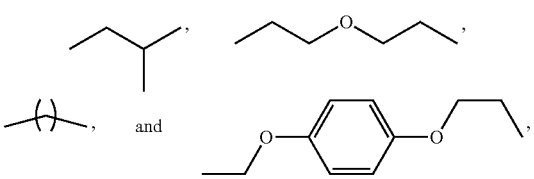

and wherein n is an integer;

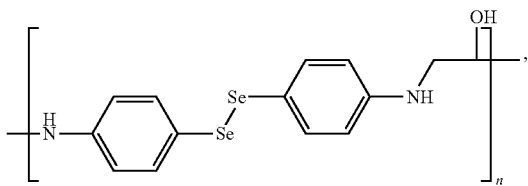

wherein n is an integer;
and combinations thereof, and wherein said film is self-healing.

In another embodiment, the present protective films may be considered self-healing smart films for metal substrates and may be fabricated or applied to the metal substrates by a dip coating method.

In a further embodiment, the present protective film coatings may reduce or prevent corrosion of metals such as steel, including particularly for preventing abrasion on steel and steel alloys. These protective film coatings can separate the metal and the hostile media by forming an isolating preservation layer provided by the organic protective film coatings. In the event that the corrosive environment changes or an external factor affects the active interface, the anticorrosion protective film coatings are self-healing and can repair any clefts formed in the active interface. In this regard, the protective film coatings can cover the exposed metal, preventing or reducing further surface corrosion caused by any corrosive ions or other external factors, providing self-healing protection systems against, by way of non-limiting example, acidic induced steel corrosion. Said protective films are effective to protect steel from corrosion and at the same time remain stable in an acidic solution. Said films may be suitable for steel protection in an acidic medium while also having the characteristics of low toxicity, easy production, and high protection efficiency.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

As used herein, the phrases "organic protective film coating", "protective film", "protective film coating", "diselenide film", and the like can be used interchangeably, one to the other, to refer to the same film and/or coating, whether in the singular or the plural.

In one embodiment, the present subject matter relates to diselenide-based organic protective film coatings. Such coatings may include a polyurea, polyurethane, and epoxy resin, or combinations thereof, and may be used as protective film coatings to prevent, inhibit or reduce metal corrosion.

In another embodiment, the compositions of diselenide-based organic protective films may each include polyurea, polyurethane, and epoxy resin and may be used as protective coating films to prevent, inhibit or reduce metal corrosion.

One general novel diselenide polyurea polymer structure useful herein is shown below.

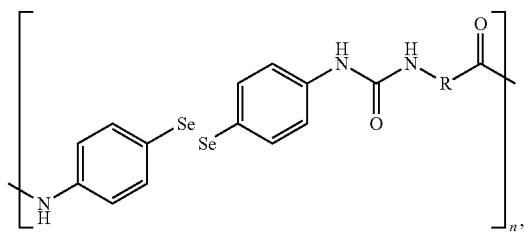

wherein each R is selected from the group consisting of any of the following structures:

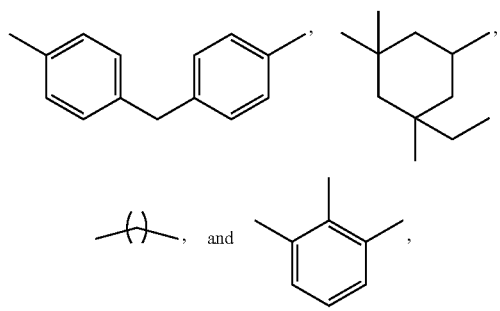

and wherein n is any integer.

In this regard, when the produced self-healing protective coating films comprises the diselenide polyurea, the diselenide polyurea film can provide a protection efficiency of about 94.6% to about 95.6%, about 95%, or 95.1%.

One general novel diselenide polyurethane polymer structure useful herein is shown below.

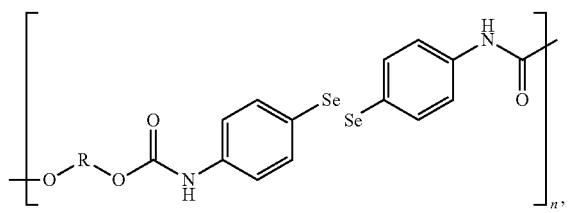

wherein each R is selected from the group consisting of any of the following structures:

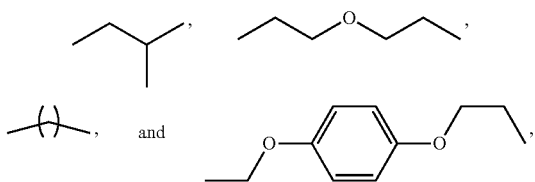

and wherein n is an integer;

In this regard, when the produced self-healing protective coating films comprises the diselenide polyurethane, the diselenide polyurethane film can provide a protection efficiency of about 95.7% to about 96.7%, about 96%, or 96.2%.

One he general novel diselenide based epoxy resin polymer structure useful herein is shown below.

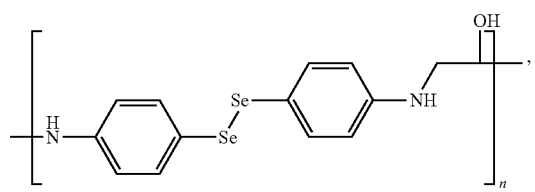

wherein n is an integer.

In this regard, when the produced self-healing protective coating films comprises the diselenide epoxy resin, the diselenide epoxy resin film can provide a protection efficiency of about 96.8% to about 97.8%, about 97%, or 97.3%.

In one embodiment in this regard, the present protective films can comprise any one, two, or three of the above polymer structures.

In an embodiment, the protective films described herein can be synthesized from a diselenide-based diamine and one of: commercially available diisocyanates, diselenide diisocyanates and phosgene, and/or diisocyanates with epichlorohydrin in the presence of potassioum hydroxide. By way of non-limiting example, the following schemes were used to produce each of the above novel diselenide polymers:

Polyureas 3 were synthesized according to Scheme 1 from the diselenide-based diamine 1 namely 4,4'-diselanediyl-dianiline and commercially available diisocyanates, and where n is an interger in all polymer structures.

Scheme 1

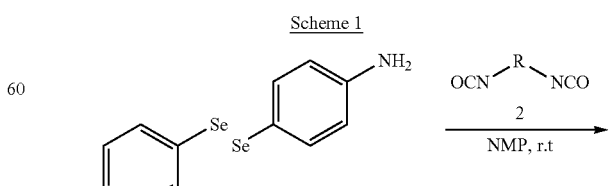

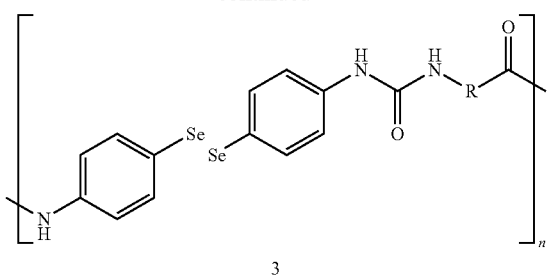

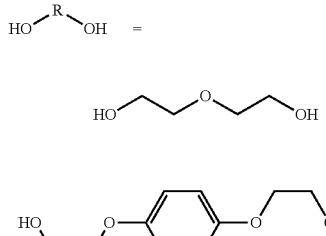

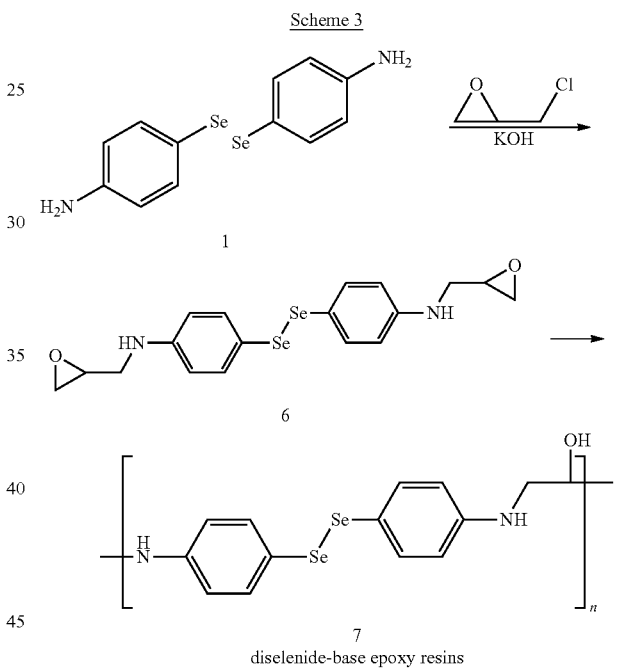

Disselenide-based epoxy resins 7 were prepared by reacting diselenide-based diamine 1 with epichlorohydrin in the presence of potassium hydroxide via nucleophilic addition where first a diselenide intermediate 6 is obtained (Scheme 3).

Polyurethanes 5 were synthesized from diselenide-based diisocyanates 4, which in turn were synthesized from the corresponding diselenide-based diamine 1 and phosgene (Scheme 2).

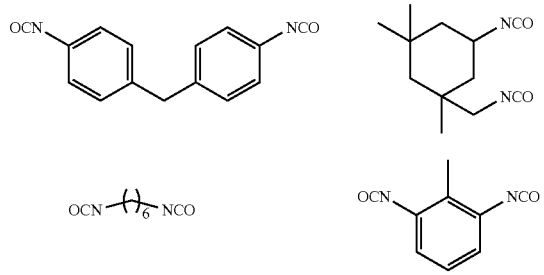

Scheme 2

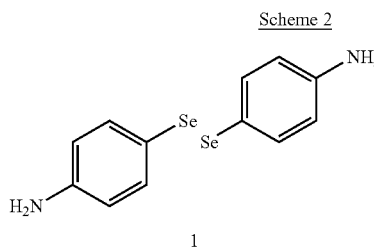

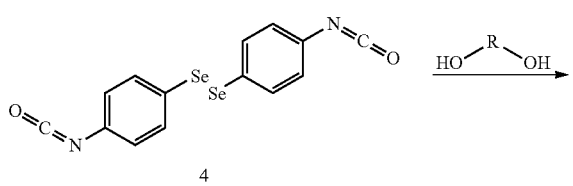

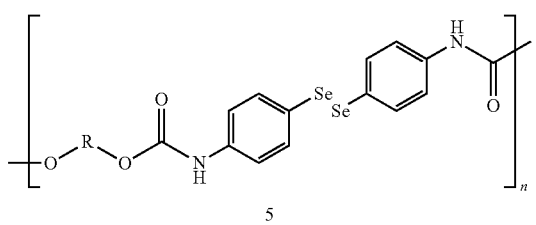

In an embodiment, the thus formed protective films may be considered self-healing smart films for metal substrates and may be fabricated or applied to the metal substrates by a dip coating method.

The protective film coatings may reduce or prevent corrosion of metals such as steel, including particularly for preventing abrasion on steel and steel alloys, for example C1018 steel or steel alloy. In this regard, the metal and the hostile media can be separated by an isolating preservation/protection layer provided by the organic film coatings. In the event that the corrosive environment changes or an external factor affects the active interface, the self-healing anticorrosion film coatings can repair any clefts formed as a result of exposure to the corrosive environment. The produced film coatings cover the exposed metal, preventing or reducing further surface corrosion caused by, by way of non-limiting example, any corrosive ions in a flowing solution, thereby providing self-healing protection systems against, for example, acidic induced steel corrosion. Said films are effective to protect steel from corrosion and at the same time remain stable in an acidic solution. Said films are suitable for steel protection in an acidic medium while also having the characteristics of low toxicity, easy production, and high protection efficiency. Polyureas, polyurethanes, and epoxy resins have general applications in biomedical, adhesive, and coating materials.

In an embodiment, the present smart protective diselenide coating films including one or more of polyureas, polyurethanes, and epoxy resin diselenides were prepared, and their structure was characterized. The protection proficiency of these produced self-healing protective coating films by electrochemical methods followed the order of diselenide epoxy resin (97.3%)> diselenide polyurethane (96.2%)> diselenide polyurea (95.1%) films. The surface morphology of coated and uncoated surfaces as assessed by FE-SEM recognized the improvement of metal surface in the case of coated films. Accordingly, polyureas, polyurethanes, and epoxy resins diselenides films can be suitable for steel protection in an acidic medium. The prepared films characteristics include low toxicity, easy production, high protection efficiency.

The anti-corrosion defensive/protective self-healing diselenide coating films were tested with C1018 carbon steel using polyurea-, polyurethane-, and epoxy resin-based diselenides. In an acidic chloride solution, the effectiveness of uncoated and coated carbon steel's resistance to corrosion was examined using an immersion test, open circuit potential (EOCP) vs. time, potentiodynamic polarization (PDP), and electrochemical impedance spectroscopy (EIS) techniques. After 72 hours of exposure, the synthesized coating films demonstrated superior resistance to the corrosion of C1018-steel with a protective capability of about 94.6% to about 97.8%, about 95% to about 97%, or 95.1-97.3%. The protection capacity of the fabricated layers is augmented in the order of epoxy resin>polyurethane>polyurea. Using a scanning electron microscope (SEM), the pristine and coated specimen's surface morphology was evaluated both before and after 72 hours of dipping in the corrosive media.

It is to be understood that the diselenide protective film composition(s), use, method of making, and properties of said diselenide protective films are not limited to the specific embodiments or examples described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A diselenide protective film comprising a diselenide polymer structure selected from the group consisting of

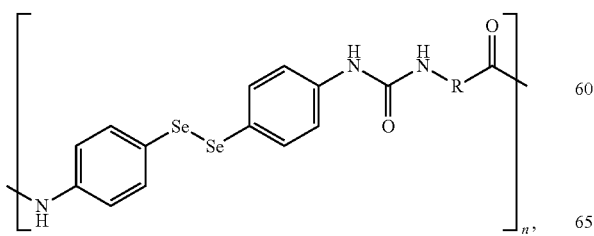

wherein each R is selected from the group consisting of any of the following structures:

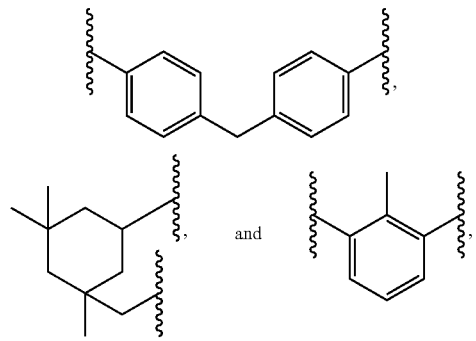

and wherein n is any integer greater than or equal to 2;

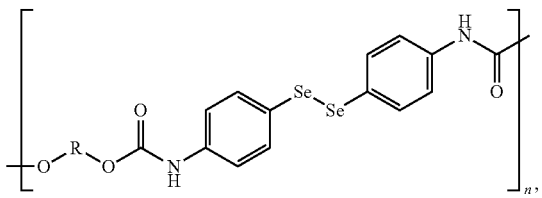

wherein each R is selected from the group consisting of any of the following structures:

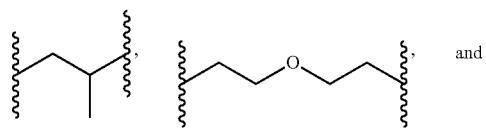

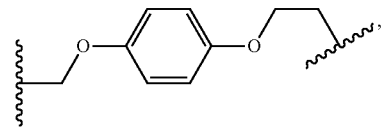

and wherein n is any integer greater than or equal to 2;

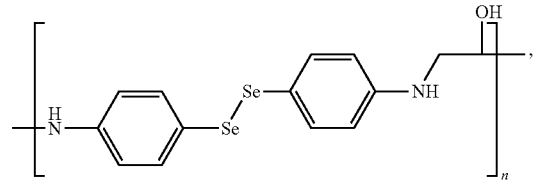

wherein n is any integer greater than or equal to 2;
and combinations thereof, and wherein said film is self-healing.

2. The diselenide protective film of claim 1 wherein the diselenide polymer structure is

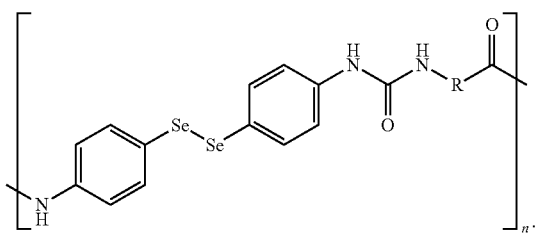

3. The diselenide protective film of claim 1 wherein the diselenide polymer structure is

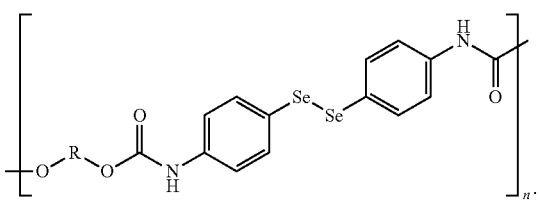

4. The diselenide protective film of claim 1 wherein the diselenide polymer structure is

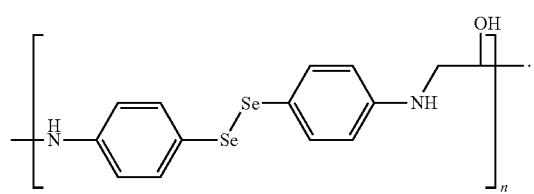

5. The diselenide protective film of claim 1 wherein the diselenide polymer structure is at least two of

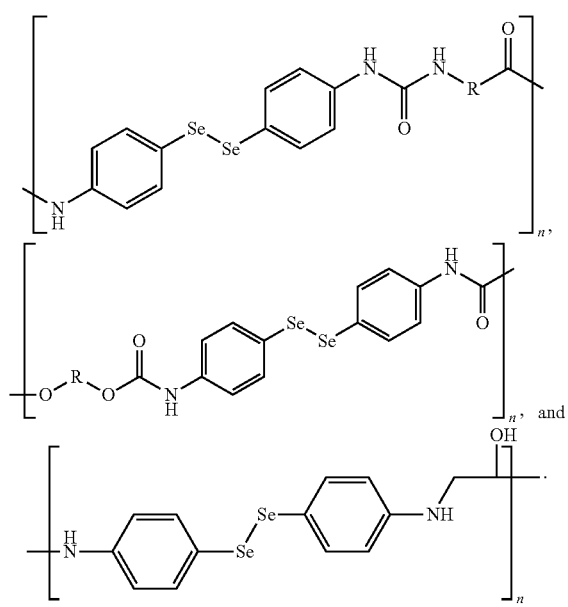

6. The diselenide protective film of claim 1 wherein when the film is applied to a metal substrate said film provides protection against corrosion of said metal substrate.

7. The diselenide protective film of claim 6, wherein the diselenide polymer structure is

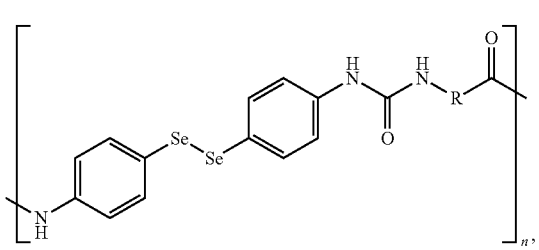

and the film provides about 95% corrosion protection.

8. The diselenide protective film of claim 6, wherein the diselenide polymer structure is

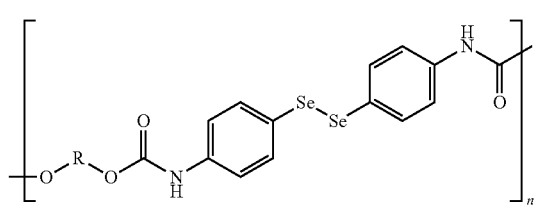

and the film provides about 96% corrosion protection.

9. The diselenide protective film of claim 6, wherein the diselenide polymer structure is

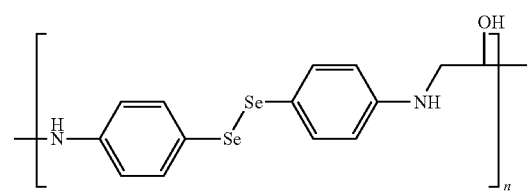

and the film provides about 97% corrosion protection.

10. A method of providing protection against corrosion of a metal substrate comprising dip coating the diselenide protective film of claim 1 onto the metal substrate.

11. The method of claim 10 wherein the metal comprises steel.

12. The method of claim 10 wherein the metal comprises carbon steel.

13. The method of claim 10 wherein the metal comprises C1018 carbon steel.

14. The method of claim 10 wherein the diselenide protective film provides about 95% protection against corrosion when the diselenide protective film comprises the diselenide polymer structure

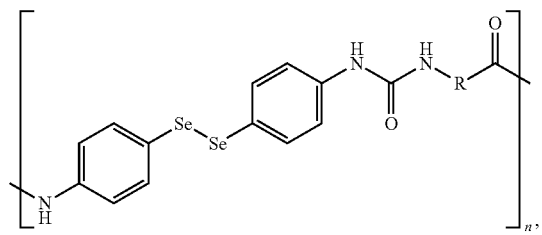

wherein n is any integer greater than or equal to 2.

15. The method of claim 10 wherein the diselenide protective film provides about 96% protection against corrosion when the diselenide protective film comprises the diselenide polymer structure

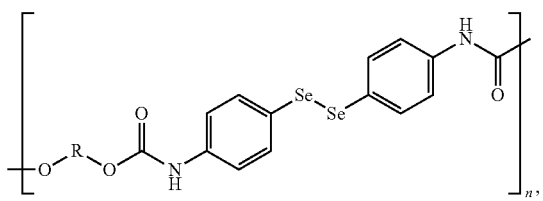

wherein n is any integer greater than or equal to 2.

16. The method of claim 10 wherein the diselenide protective film provides about 97% protection against corrosion when the diselenide protective film comprises the diselenide polymer structure

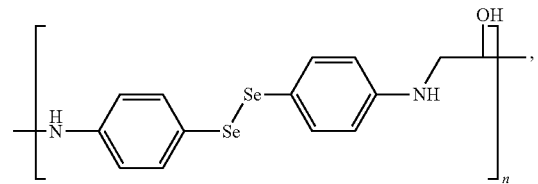

wherein n is any integer greater than or equal to 2.

17. The method of claim 10 wherein the corrosion is acidic induced corrosion.

* * * * *